United States Patent
Massonne et al.

(10) Patent No.: US 8,382,962 B2
(45) Date of Patent: Feb. 26, 2013

(54) DISTILLATION OF IONIC LIQUIDS

(75) Inventors: Klemens Massonne, Bad Duerkheim (DE); Michael Siemer, Mannheim (DE); Werner Mormann, Siegen (DE); Wei Leng, Lemfoerde (DE)

(73) Assignee: BASF SE, Ludwigshafen (DE)

(*) Notice: Subject to any disclaimer, the term of this patent is extended or adjusted under 35 U.S.C. 154(b) by 414 days.

(21) Appl. No.: 12/675,445

(22) PCT Filed: Aug. 15, 2008

(86) PCT No.: PCT/EP2008/060743
§ 371 (c)(1),
(2), (4) Date: Feb. 26, 2010

(87) PCT Pub. No.: WO2009/027250
PCT Pub. Date: Mar. 5, 2009

(65) Prior Publication Data
US 2010/0300870 A1    Dec. 2, 2010

(30) Foreign Application Priority Data
Aug. 31, 2007  (DE) .......................... 10 2007 041 416

(51) Int. Cl.
*B01D 3/00* (2006.01)
(52) U.S. Cl. ................. 203/89; 203/2; 203/98; 203/100
(58) Field of Classification Search ............... 203/2, 89, 203/98, 100; 548/341.1, 343.5, 345.1, 346.1
See application file for complete search history.

(56) References Cited

U.S. PATENT DOCUMENTS
5,077,414 A * 12/1991 Arduengo, III ............ 548/335.1
6,939,974 B2 * 9/2005 Earle et al. ................. 548/347.1
(Continued)

FOREIGN PATENT DOCUMENTS
DE    103 33 239    3/2005
WO    91 14678    10/1991
(Continued)

OTHER PUBLICATIONS
U.S. Appl. No. 12/747,372, filed Jun. 10, 2010, Degen, et al.
(Continued)

*Primary Examiner* — Duane Smith
*Assistant Examiner* — Ives Wu
(74) *Attorney, Agent, or Firm* — Oblon, Spivak, McClelland, Maier & Neustadt, L.L.P.

(57) ABSTRACT

A method of distilling mixtures of salts having a melting point of less than 200° C. at 1 bar (ionic liquids). The cation of the ionic liquid has a heterocyclic ring system having at least one nitrogen atom, and all nitrogen atoms of the heterocyclic ring system have an organic group as substituent. The anion of the ionic liquid is a compound having at least one carboxylate group or at least one phosphate group. The distance from the surface via which the heat of distillation is introduced in the distillation (vaporizer surface) to the surface at which condensation takes place (condenser surface) is less than 50 cm at at least one point, with the vaporizer surface and condenser surface themselves having at least one length dimension of greater than 50 cm.

15 Claims, 1 Drawing Sheet

U.S. PATENT DOCUMENTS

| | | | |
|---|---|---|---|
| 7,351,339 B2 * | 4/2008 | Maase et al. | 210/638 |
| 7,754,053 B2 * | 7/2010 | Maase | 203/2 |
| 2007/0095645 A1 | 5/2007 | Maase | |
| 2010/0137643 A1 | 6/2010 | Tishkov et al. | |
| 2011/0297530 A1 * | 12/2011 | Forster et al. | 203/38 |

FOREIGN PATENT DOCUMENTS

| | | |
|---|---|---|
| WO | 03 029329 | 4/2003 |
| WO | 2005 021484 | 3/2005 |
| WO | 2005 068404 | 7/2005 |

OTHER PUBLICATIONS

MacFarlane, Douglas R. et al., "Lewis base ionic liquids", Chem. Commun., pp. 1905-1917, XP-002483141, (Mar. 3, 2006).

He, Xun et al., "Ionic-Tag-Assisted Oligosaccharide Synthesis", Synthesis, No. 10, pp. 1645-1651, EXP-002521376, (2006).

Earle, Marlyn J. et al., "The distillation and volatility of ionic liquids", Nature, vol. 439, pp. 831-834, (Feb. 16, 2006).

* cited by examiner

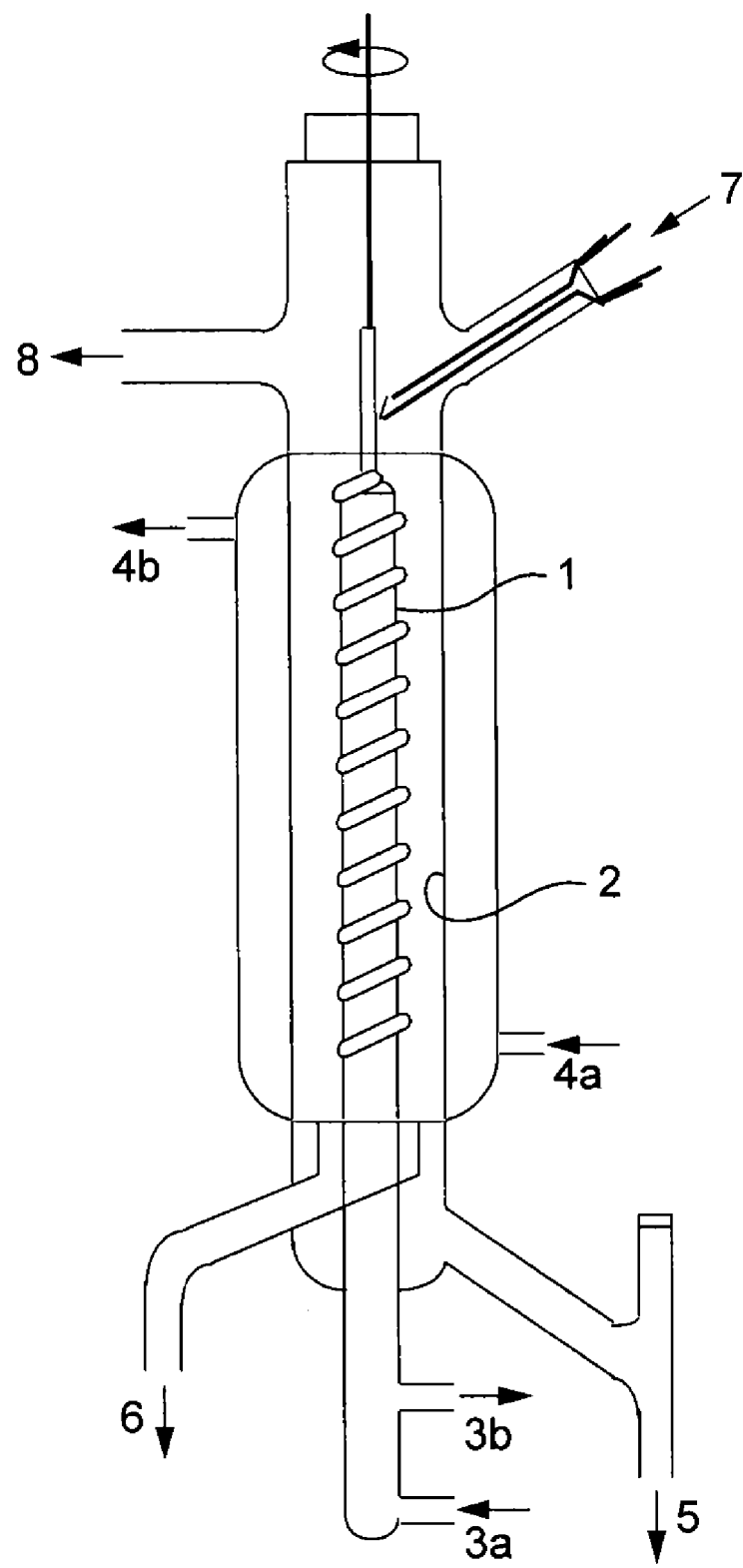

sive processes for preparing ionic liquids are known, but these form relatively nonvolatile by-products, the reaction products obtained are discolored because of these by-products and generally appear black. Such processes are described, for example, in WO 2005/021484 (carbonate method) or in WO 91/14678 (Arduengo process). Here too, there is a need for particularly effective and advantageous methods of working up and separating the ionic liquids from the mixtures obtained in the preparation.

DISTILLATION OF IONIC LIQUIDS

BRIEF SUMMARY OF THE INVENTION

The invention relates to a method of distilling mixtures comprising salts having a melting point of less than 200° C. at 1 bar (ionic liquids), wherein
- the cation of the ionic liquid comprises a heterocyclic ring system having at least one nitrogen atom and all nitrogen atoms of the heterocyclic ring system have an organic group as substituent,
- the anion of the ionic liquid is a compound having at least one carboxylate group (carboxylate for short) or at least one phosphate group (phosphate for short) and
- the distance from the surface via which the heat of distillation is introduced in the distillation (vaporizer surface) to the surface at which condensation takes place (condenser surface) is less than 50 cm at least one point, with the vaporizer surface and condenser surface themselves having at least one length dimension of greater than 50 cm.

BACKGROUND OF THE INVENTION

Salts having a melting point of less than 200° C., in particular a melting point of less than 100° C., are referred to as ionic liquids. Ionic liquids which are liquid at room temperature are of particular interest. It was believed for a long time that such ionic liquids could not be distilled, since it was assumed that they ultimately have no vapor pressure.

In February 2006, Martyn J. Earle, Jose M. S. S. Esperanca et al published an article about the distillation of volatile ionic liquids in a bulb tube apparatus in Nature, Vol. 439, 2006, pages 831 to 834. However, ionic liquids comprising halides, sulfates or carboxylates decompose and could not be distilled.

WO 2005/068404 describes the distillation of ionic liquids, including those having halides and acetates as anion. A significant aspect here is that the ionic liquids can, owing to an equilibrium reaction, also be present as neutral compounds, i.e. not as salt. As a result of the distillation, these neutral compounds are removed. Continual restoration of the equilibrium state results in the entire ionic liquid distilled in the form of the neutral compounds. In the case of ionic liquids having nitrogen-comprising, heterocyclic ring systems as cation and, for example, halides or carboxylates as anion, a corresponding equilibrium state can be established if at least one nitrogen atom of the ring system is not substituted by an organic group and is thus available for an equilibrium reaction of the anion. Accordingly, only the chlorides of 1-ethylimidazole or 1-methylimidazole are distilled in the examples of WO 2005/068404.

Douglas R. MacFarlane, Jennifer M. Pringle et al., Chem. Commun., 2006, pages 1905 to 1917, also disclose a distillation of ionic liquids. Here, the ability to be distilled is based on an equilibrium reaction in which the cation and anion of the ionic liquid are present as neutral acid and base. As indicated above, the neutral compounds are withdrawn from the equilibrium state and distilled. In this way, it is possible to distill imidazolium acetates in which a nitrogen atom of the heterocyclic ring system is present in protonated form (HMIM acetate in Table 4 of the article).

Ionic liquids are generally not consumed but only contaminated during use. Since they are high-priced materials, there is a need for particularly effective and advantageous methods of working up and separating the anionic liquids from the mixtures obtained in use. When ionic liquids are used for dissolving cellulose, mixtures comprising lignins or cellulose derivatives, for example, are formed. Furthermore, inexpensive processes for preparing ionic liquids are known, but these form relatively nonvolatile by-products, the reaction products obtained are discolored because of these by-products and generally appear black. Such processes are described, for example, in WO 2005/021484 (carbonate method) or in WO 91/14678 (Arduengo process). Here too, there is a need for particularly effective and advantageous methods of working up and separating the ionic liquids from the mixtures obtained in the preparation.

It is therefore an object of the present invention to provide a simple and effective method of purifying or working up ionic liquids or the mixtures obtained in their preparation and/or use.

We have accordingly found the method defined at the outset.

BRIEF DESCRIPTION OF THE DRAWING

The FIGURE is a schematic diagram of an apparatus used to perform the distillation method of the invention.

DETAILED DESCRIPTION OF THE INVENTION

Ionic Liquid

The ionic liquid according to the invention is a salt which is composed of at least one cation and at least one anion and has a melting point at atmospheric pressure (1 bar) of less than 200° C., in particular less than 100° C., preferably less than 75° C. It is very particularly preferably a salt which is liquid at room temperature (21° C.) and atmospheric pressure (1 bar).

The cation of the ionic liquid is, according to the invention, a heterocyclic ring system having at least one nitrogen atom as constituent of the ring system. All nitrogen atoms of the ring system bear an organic group as substituent. Protonation of these nitrogen atoms is therefore not possible. The substituent is preferably an organic group which comprises from 1 to 20 carbon atoms, in particular from 1 to 10 carbon atoms. It is particularly preferably a hydrocarbon group which has no further heteroatoms, e.g. a saturated or unsaturated aliphatic group, an aromatic group or a hydrocarbon group which has both aromatic and aliphatic parts. It is very particularly preferably a C1-C10-alkyl group, C1-C10-alkenyl group, e.g. an allyl group, a phenyl group or a benzyl group.

In a particular embodiment, the substituent is a C1-C10-, in particular C1-C4-alkyl group, e.g. a methyl group, ethyl group, propyl group, i-propyl group, n-butyl group.

The heterocyclic ring system is preferably an aromatic heterocyclic ring system.

The cation is preferably a derivative of imidazolium, of pyrazolium or of pyridinium.

The cation is particularly preferably a derivative of imidazolium.

The anion of the ionic liquid is a compound having at least one carboxylate group (carboxylate for short) or at least one phosphate group (phosphate for short).

As phosphates, mention may be made of $PO_4^{3-}$ or organic compounds having a phosphate group, in particular dialkylphosphates. Particularly preferred phosphates are C1-C4-dialkylphosphates, e.g. dimethylphosphate and in particular diethylphosphate.

Preferred anions are carboxylates.

As carboxylates, particular mention may be made of organic compounds which have from 1 to 20 carbon atoms, preferably from 1 to 10 carbon atoms, and comprise from one to three carboxylate groups, preferably one or two carboxylate groups, particularly preferably one carboxylate group.

The compounds can be either aliphatic or aromatic compounds, with the term aromatic compounds referring to compounds which comprise aromatic groups. The aliphatic or aromatic compounds can, if appropriate, comprise further functional groups, e.g. hydroxyl groups, carbonyl groups or ether groups, or other heteroatoms, in particular halogens such as fluorine, chlorine or bromine, preferably fluorine, as substituent.

Very particular preference is given to aliphatic or aromatic compounds which do not comprise any further functional groups or heteroatoms apart from the oxygen atoms of the carboxylate group.

As compounds having two carboxylate group, mention may be made of, for example, the anions of phthalic acid, of isophthalic acid, of C2-C6-dicarboxylic acids, e.g. oxalic acid, malonic acid, succinic acid, glutaric acid or adipic acid.

As compounds having one carboxylate group, mention may be made of the anions of aromatic, aliphatic, saturated or unsaturated C1-C20-carboxylic acids, in particular alkanecarboxylic acids, alkenecarboxylic acids, alkynecarboxylic acids, alkadienecarboxylic acids, alkatrienecarboxylic acids, hydroxycarboxylic acids or ketocarboxylic acids. Suitable alkanecarboxylic acids, alkenecarboxylic acids and alkadienecarboxylic acids are also known as fatty acids.

Very particularly preferred carboxylates are the anions of C1-C10-alkanecarboxylic acids, in particular C1-C6-alkanecarboxylic acids, very particularly preferably acetic acid (acetate) and propionic acid (propionate).

Accordingly, the ionic liquid is particularly preferably an imidazolium salt of the formula I

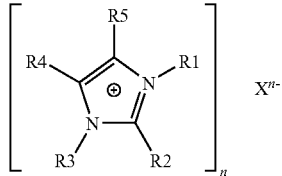

where

R1 and R3 are each, independently of one another, an organic radical having from 1 to 20 carbon atoms, R2, R4, and R5 are each, independently of one another, an H atom or an organic radical having from 1 to 20 carbon atoms, X is a carboxylate or phosphate and n is 1, 2 or 3.

Preference is given to R1 and R3 each being, independently of one another, an organic group comprising from 1 to 10 carbon atoms. The group is particularly preferably a hydrocarbon group which has no further heteroatoms, e.g. a saturated or unsaturated aliphatic group, an aromatic group or a hydrocarbon group which has both aromatic and aliphatic parts. The group is very particularly preferably a C1-C10-alkyl group, a C1-C10-alkenyl group, e.g. an allyl group, a phenyl group, a benzyl group. In particular, the group is a C1-C4-alkyl group, e.g. a methyl group, ethyl group, propyl group, i-propyl group or n-butyl group.

Preference is given to R2, R4 and R5 each being, independently of one another, an H atom or an organic group comprising from 1 to 10 carbon atoms. R2, R4 and R5 are particularly preferably each an H atom or a hydrocarbon group which does not have any further heteroatoms, e.g. an aliphatic group, an aromatic group or a hydrocarbon group which has both aromatic and aliphatic parts. Very particular preference is given to an H atom or a C1-C10-alkyl group, a phenyl group or a benzyl group. Special preference is given to an H atom or a C1-C4-alkyl group, e.g. a methyl group, ethyl group, propyl group, i-propyl group or n-butyl group.

In a particular embodiment, R2 is not an H atom but has to be an organic radical as mentioned above having from 1 to 20 carbon atoms, in particular a C1-C4-alkyl group.

n is preferably 1.

X is preferably a carboxylate, particularly preferably acetate or propionate.

As ionic liquids which are particularly suitable for the method of the invention, mention may be made of those having 1,3-dialkylimidazolium and 1,2,3-trialkylimidazolium cations (where alkyl=C1-C8) and an acetate or propionate anion, preferably an acetate anion.

Very particular preference is given to the propionates and in particular acetates of 1-methyl-3-ethylimidazolium, 1,3-diethylimidazolium, 1,3-dimethylimidazolium, 1-methyl-3-butylimidazolium and 1-ethyl-2,3-dimethylimidazolium.

Their Mixtures

The mixtures to be distilled comprise the ionic liquids in any amount. However, the content of ionic liquid in the mixture is preferably at least 5% by weight, particularly preferably at least 10% by weight, very particularly preferably at least 20% by weight, based on the total mixture; the process is also particularly suitable for mixtures having a content of at least 30 or 40% by weight of ionic liquid.

The content of ionic liquid is generally not greater than 95% by weight, usually not greater than 90% by weight or not greater than 80% by weight.

The ionic liquids can be present entirely or partly in dissociated form or in undissociated form (cation/anion pair formation). For carrying out the method of the invention, it is immaterial whether pair formation of anions and cations of the ionic liquid occurs in the liquid phase or whether the ionic liquid is present entirely or partly in dissociated form, e.g. in the presence of water or another hydrophilic or protic solvent.

Suitable mixtures for the method of the invention are, for example, mixtures comprising impurities and by-products resulting from the production process or the use of the ionic liquid.

The mixtures comprise, in particular, constituents having a boiling point above 200° C. (1 bar) as impurities, e.g. salts such as alkali metal acetates or natural or synthetic oligomeric or polymeric compounds such as lignin, hemicellulose or oligosaccharides.

Mixtures from the Production Process

There are various processes for preparing ionic liquids. These processes usually give mixtures which comprise not only the ionic liquid but also undesirable by-products, starting materials and other impurities.

Mixtures suitable for the method of the invention are, for example, those obtained in the preparation of imidazolium salts by single-stage or multistage reaction of starting compounds selected from among: α-dicarbonyl compounds, amino compounds, carbonyl compounds, ammonia and carbonate compounds.

One production process is, for example, the carbonate method which is described in WO 2005/021484.

In the carbonate method, imidazolium salts are obtained by reacting an α-dicarbonyl compound, a carbonyl compounds (generally formaldehyde), an amino compound and ammonia in a first stage and subsequently reacting the reaction product with a carbonate (generally dimethyl carbonate) in a second stage. The mixture obtained after the first stage comprises by-products which make the total mixture appear dark to black.

Mixtures which are obtained after the first stage or after the second stage of the abovementioned production process are suitable for the method of the invention.

A further process for preparing imidazolium salts is described by Arduengo et al. (WO 91/14678, Arduengo process). In this single-stage process, the imidazolium salts are prepared by reacting an α-dicarbonyl compound, a carbonyl compound (generally formaldehyde) and an amino compound in the presence of an acid. Here too, the mixture obtained is dark to black because of by-products.

Mixtures obtained by this production process are suitable for the method of the invention.

Mixtures from Use

Mixtures obtained in the use of ionic liquids are likewise suitable for the method of the invention.

Ionic liquids are generally not consumed but only contaminated during use.

The use of ionic liquids therefore gives mixtures which comprise ionic liquids and impurities from the respective use. These mixtures can be worked up again by the method of the invention, so that the ionic liquid can be reused.

Ionic liquids are frequently used as solvents for substances which are insoluble or only sparingly soluble in other solvents. Ionic liquids are suitable, for example, as solvents for cellulose and cellulose-comprising materials. After the respective use of the solution, e.g. for producing cellulose fibers from the solution, mixtures which comprise ionic liquids and, for example, still some cellulose, lignin, hemicelluloses are obtained. The method of the invention is therefore particularly useful for mixtures which are obtained by dissolution and processing of cellulose or cellulose-comprising materials.

General Comments on Mixtures

The mixtures used in the method of the invention preferably comprise only minor amounts of volatile compounds.

For the present purposes, volatile compounds are compounds having a boiling point of less than 120° C., in particular less than 150° C., at atmospheric pressure (1 bar).

The content of volatile compounds is preferably from 0 to 10% by weight, in particular from 0 to 5% by weight and particularly preferably from 0 to 2% by weight, based on the mixture.

If volatile compounds are initially present in the mixture, they are preferably largely removed so that their content in the mixture is not more than 10% by weight, in particular not more than 5% by weight, in particular not more than 2% by weight (see above), and are particularly preferably removed completely before carrying out the method of the invention.

The addition of a strong base as is described, for example, in DE 103 33 239 for producing purified imidazolium salts is not necessary according to the present invention. It is therefore preferred that no such strong base ($pK_B$ less than 0 at 1 bar, 21° C., measured in water) or no base at all is added to the mixture.

Distillation

An important feature of the distillation method of the invention is that the distance from the surface via which the heat of distillation is introduced in the distillation (vaporizer surface, 1 in the FIGURE) to the surface at which condensation takes place (condenser surface, 2) is less than 50 cm at at least one point.

The vaporizer surface is heated in a suitable way (3a, 3b), generally by means of devices on the rear side; the condenser surface is generally cooled correspondingly (4a, 4b), likewise by means of devices on the rear side.

Distillation methods having a small distance between vaporizer surface and condenser surface are referred to as molecular distillation. In molecular distillation, the distance between vaporizer surface and condenser surface is generally less than the mean free path length of the compounds to the distilled. For this purpose, the geometry of the apparatus and the process parameters (pressure and temperature) are selected appropriately.

Any geometric arrangement of the condenser surface relative to the vaporizer surface in the apparatus is possible. The important thing is that these surfaces are directly opposite one another so that the molecules can travel unhindered from the vaporizer surface to the condenser surface.

Possibilities are, for example, parallel arrangement of two planar surfaces or a cylindrical arrangement in which two cylinders are placed within one another and the surfaces of the two cylinders which are directly opposite one another form the vaporizer and condenser surfaces.

The vaporizer surface is heated in a suitable way, generally by means of devices on the rear side; the condenser surface is generally cooled correspondingly, likewise by means of devices on the rear side.

The distance from the vaporizer surface to the condenser surface is less than 50 cm at at least one point, in particular less than 40 cm, particularly preferably less than 30 cm.

The distance from the vaporizer surface to the condenser surface is, in particular, less than the mean free path length of the ionic liquid in the gas phase at the chosen temperature and chosen pressure. The mean free path length ($\lambda_M$) can be determined by known methods and is given by the equation:

$$\lambda_M = \text{const} \times T/(p_\sigma^2)$$

where the symbols have the following meanings:

T: Temperature
P: Pressure
σ: Collision cross section of the ion pair (ionic liquid), corresponds to cross-sectional area of the ion pair Preferred suitable apparatuses are configured so that at least 10 percent by area, particularly preferably at least 20 percent by area, very particularly preferably at least 30 or even at least 50 percent by area, of the vaporizer surface have the above minimum distance from the condenser surface.

The vaporizer surface and the condenser surface can each be larger than 0.5 $m^2$, e.g. in the case of industrial-scale apparatuses.

In the method of the invention, the ionic liquid is separated off from the mixture (7) and taken off as distillate from the condenser surface. The residue remains on the vaporizer surface. Suitable apparatuses are, for example, configured so that the residue runs off from the vaporizer surface and is collected (6), and the ionic liquid correspondingly runs off from the condenser surface and is obtained as distillate (5).

The surface temperature of the vaporizer and the pressure are preferably selected so that the distance between vaporizer surface and condenser surface is smaller than the free path length of the ionic liquid to be separated off in the gas phase.

The surface temperature is preferably from 110 to 300° C., particularly preferably from 130 to 280° C. and very particularly preferably from 140° C. to 260° C.

The pressure in the region between vaporizer surface and condenser surface is preferably from 0.0001 to 10 mbar, preferably from 0.001 to 5 mbar, particularly preferably from 0.05 to 5 mbar.

The distillate obtained can, for example, comprise more than 95% by weight, particularly preferably more than 97% by weight, very particularly preferably more than 99% by weight, of the ionic liquid. In particular, distillates comprising more than 99.5% by weight or more than 99.8% by weight of the ionic liquid can also be obtained by means of the method.

It is therefore possible to obtain ionic liquids in high purity from any mixtures by means of the method of the invention.

The method can be carried out continuously or batchwise.

EXAMPLES

Ionic Liquids (ILs) Used

Abbreviations Chemical name
  BMIM OAc 1-Butyl-3-methylimidazolium acetate
  EMIM OAc 1-Ethyl-3-methylimidazolium acetate
  EEIM OAc 1,3-Diethylimidazolium acetate
  BMIM OProp 1-Butyl-3-methylimidazolium propionate
  BMIM Cl 1-Butyl-3-methylimidazolium chloride
  EMIM DEP 1-Ethyl-3-methylimidazolium diethylphosphate The IL is freed of low boilers by stirring at 120° C. and 0.1 mbar for 16 hours before all distillation experiments in order to avoid foaming and spraying during the molecular distillation.

The experimental set-up is shown in the FIGURE. The distillate runs down on the condenser surface (2) and is collected at the bottom (5), while the residue correspondingly runs down on the vaporizer surface (1) and is collected at the bottom (6).

Example 1

Determination of the Distillation Temperature for EMIM OAc

About 100 ml of EMIM OAc are introduced into the feed vessel for the molecular distillation, the apparatus is made inert by means of nitrogen and a vacuum (8) of 0.05 mbar is applied. The vaporizer surface is heated to the temperature indicated and introduction of the feed is commenced at a rate of about 50 ml/h.

After all the EMIM OAc has run in, the apparatus is cooled, nitrogen is admitted and the weight ratio of distillate to residue and also the purity of both parts are determined by H-NMR and the mass of decomposition products in the cold trap.

The conditions are considered to be suitable when the mass ratio of distillate to residue is at least 8:2 and less than 10% of the starting material has been decomposed. In principle, the degree of distillation can be increased at a given pressure by increasing the temperature (upper limit: excessive thermal decomposition) or at a given temperature by reducing the pressure (technical limits imposed by minimum pressure which can be achieved.

For EMIM OAc, the following results were obtained:

| Temp. of vaporizer ° C. | Distillate Mass in g | Distillate Purity (H_NMR) | Residue Mass in g | Residue Purity (HNMR) |
|---|---|---|---|---|
| 100 | <1 | >95% | 115 | >95% |
| 130 | 45 | >95% | 55 | >95% |
| 150 | 96 | >95% | 20 | >95% |
| 170 | 108 | >95% | 10 | >95% |

In none of the experiments was distillate found in the cold trap to the vacuum pump.

Example 2

Distillation of EEIM OAc

Crude EEIM OAc is prepared by reaction of formaldehyde, glyoxal and ethylamine in water comprising acetic acid and freed of low boilers by evaporation first at 10 mbar/80° C. and then as described above at 0.1 mbar/120° C. The crude product is dark brown.

200 g of this crude product are fed into the molecular distillation at 0.05 mbar and a wall temperature 170° C. (vaporizer surface) over a period of 2 hours.

190 g of clear colorless distillate, which according to H-NMR is pure (>95%) EEIM OAc, and 10 g of a black, tar-like residue are obtained. No volatile constituents are collected in the cold trap.

Example 3

Distillation of EMIM OAc 200 g of EMIM OAc which has previously been used five times for the dissolution of cellulose (pulp from Tembec Inc. type 10A) and recovery of the cellulose by dilution with 10 times its amount of water (see WO 03/029329) are used as starting material. After each precipitation, the EMIM OAc was recovered from the aqueous supernatant solution by distilling off the water at 120° C./1 mbar and was reused without further purification. It was freed of low boilers as described above before the molecular distillation.

The EMIM OAc fed to the distillation comprises about 6% by weight of secondary component (e.g. lignin) from the cellulose and is yellowish brown (Gardener color number=16).

200 g of this EMIM OAc are introduced into the molecular distillation at 0.05 mbar and a wall temperature of 170° C. over a period of 4 hours.

170 g of clear colorless EMIM OAc which according to H-NMR has a purity of >95% are obtained as distillate.

30 g of a black, tar-like material which is not characterized further are obtained as residue.

Example 4

Distillation of Various ILs

About 100 g in each case of the IL indicated in the table are introduced into the molecular distillation at 0.05 mbar and the wall temperature indicated over a period of 2 hour. The mass ratio of distillate to residue was determined.

| IL | Wall temp. ° C. | Distillate % by weight | Residue % by weight | |
|---|---|---|---|---|
| BMIM OAc | 170 | 90 | 10 | Both >95% BMIM OAc (H-NMR) |
| EEIM OAc | 170 | 90 | 10 | Both >95% EEIM OAc (H-NMR) |
| BMIM OProp | 170 | 90 | 10 | Both >95% BMIM OProp (H-NMR) |
| EMIM DEP | 170 | 0 | 100 | Both >95% EMIM DEP (H-NMR) |

-continued

| IL | Wall temp. °C. | Distillate % by weight | Residue % by weight | |
|---|---|---|---|---|
| EMIM DEP | 240 | 12 | 88 | Both >95% EMIM DEP (H-NMR) |
| EMIM DEP | 250 | 54 | 46 | Both >95% EMIM DEP (H-NMR) |
| BMIM Cl * | 170 | 0 | 100 | >95% BMIM Cl (H-NMR) |
| BMIM Cl * | 250 | 13 | 85 | Distillate >50% of butylimidazole and ethylimidazole |

The invention claimed is:

1. A method of distilling an ionic liquid, comprising:
distilling an ionic liquid to obtain a distillate, wherein said ionic liquid comprises a mixture of salts having a melting point of less than 200° C. at 1 bar
the cation of the ionic liquid comprises a heterocyclic ring system having at least one nitrogen atom and all nitrogen atoms of the heterocyclic ring system have an organic group as substituent,
the anion of the ionic liquid is a compound having at least one carboxylate group or at least one phosphate group and
the distance from the vaporizer surface via which the heat of distillation is introduced in the distilling to the condenser surface at which condensation takes place is less than 50 cm at at least one point, with the vaporizer surface and condenser surface themselves having at least one length dimension of greater than 50 cm.

2. The method according to claim 1, wherein the cation is an imidazolium cation.

3. The method according to claim 1, wherein the substituents on the nitrogen atoms in the heterocyclic ring system are C1-C10-alkyl groups.

4. The method according to claim 1, wherein the ionic liquid is an imidazolium salt represented by formula I

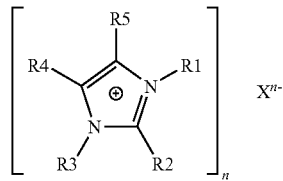

where
R1 and R3 are each, independently of one another, an organic radical having from 1 to 20 carbon atoms,
R2, R4, and R5 are each, independently of one another, an H atom or an organic radical having from 1 to 20 carbon atoms,
X is a carboxylate and
n is 1, 2 or 3.

5. The method according to claim 4, wherein R2 is an organic radical having from 1 to 20 carbon atoms.

6. The method according to claim 1, wherein the mixture comprises from 10 to 95% by weight of the ionic liquid.

7. The method according to claim 1, wherein the mixture is obtained in the preparation of ionic liquids by single-stage or multistage reaction of starting compounds selected from the group consisting of: an α-dicarbonyl compound, an amino compound, a carbonyl compound, ammonia, and a carbonate compound.

8. The method according to claim 1, wherein the mixture is obtained from ionic liquids.

9. The method according to claim 1, wherein the mixture comprises at least one further constituent having a boiling point above 200° C. (1 bar) as impurities, wherein said further constitute is a salt such as alkali metal acetates or natural or synthetic oligomeric or polymeric compounds such as lignin, hemicellulose or oligosaccharide.

10. The method according to claim 1, wherein the mixture comprises at least one constituent having a boiling point lower than the boiling point of the ionic liquid (more volatile compounds) in amounts of from 0 to 10% by weight.

11. The method according to claim 1, wherein more volatile compounds are separated off beforehand so that their proportion in the mixture is not more than 10% by weight.

12. The method according to claim 1, wherein at least 10 percent by area of the vaporizer surface is at a distance of less than 50 cm from the condenser surface.

13. The method according to claim 1, wherein the vaporizer surface and the condenser surface are each larger than 0.5 m².

14. The method according to claim 1, wherein the distillation is carried out at a surface temperature of the vaporizer of from 110° C. to 300° C. and a pressure of from 0.0001 to 10 mbar.

15. The method according to claim 1, wherein the distillate obtained comprises more than 97% by weight of the ionic liquid.

* * * * *